United States Patent [19]

Chatzipetros et al.

[11] Patent Number: 4,644,761
[45] Date of Patent: Feb. 24, 1987

[54] LOW-TEMPERATURE GONIOMETER FOR X-RAY AND NEUTRON DIFFRACTOMETRY

[75] Inventors: Johann Chatzipetros, Frechen; Bernhard Dujka, Jülich; Frank Elf, Kaarst; Georg Will, Swisttal-Buschoven, all of Fed. Rep. of Germany

[73] Assignee: Kernforschungsanlage Julich Gesellschaft mit beschrankter Haftung, Jülich, Fed. Rep. of Germany

[21] Appl. No.: 699,731

[22] Filed: Feb. 8, 1985

[30] Foreign Application Priority Data

Aug. 11, 1984 [DE] Fed. Rep. of Germany .................. 84239093[U]

[51] Int. Cl.⁴ .................................... F25B 19/00
[52] U.S. Cl. ............................ 62/514 R; 62/376; 378/81
[58] Field of Search ............. 378/80, 81; 62/376, 62/514 R

[56] References Cited

U.S. PATENT DOCUMENTS

| | | | |
|---|---|---|---|
| 3,566,112 | 8/1971 | Luecke | 378/81 |
| 3,619,610 | 11/1971 | Politis | 378/80 |
| 3,728,541 | 4/1973 | Rabinovich et al. | 378/81 |
| 3,839,635 | 10/1974 | Chan et al. | 378/80 |
| 3,860,815 | 1/1975 | Hall | 378/81 |
| 3,992,624 | 11/1976 | Flannery et al. | 378/80 |
| 4,141,224 | 2/1979 | Alger et al. | 62/376 |
| 4,407,136 | 10/1983 | de Kanter | 62/514 R |

OTHER PUBLICATIONS

Troitskaya, Z. V. et al.: "High Pressure X-Ray Camera for Taking Photographs at Temperatures Down to 120°K." Instrum. Exper. Tech. (USA) No. 4 (Jul., Aug., 1969) pp. 1017-1019.

Boiko, A. A. et al.: "Helium Cryostate in a Diffractometer for Structural Research" Instrum. Exper. Tech. (USA) vol. 15, No. 3 (May, Jun. 1972) pp. 929-931.

Primary Examiner—Ronald C. Capossela
Attorney, Agent, or Firm—Karl F. Ross; Herbert Dubno

[57] ABSTRACT

An Euler's goniometer for low-temperature diffractometry is rotatable about two turning circles and is arranged within a chamber filled with a coolant. Each of the turning circles - that is the chi-circle and the phi-circle - is constituted by a worm wheel which is driven in a stepwise manner by a worm and a stepper motor driving the worm. For providing a compact construction, the stepper motors and the actuated worms are arranged within the chamber as well.

16 Claims, 3 Drawing Figures

LOW-TEMPERATURE GONIOMETER FOR X-RAY AND NEUTRON DIFFRACTOMETRY

FIELD OF THE INVENTION

Our present invention relates to an Euler's cradle and, more particularly, to an Euler's two-circle goniometer for low-temperature X-ray and/or neutron diffractometry.

BACKGROUND OF THE INVENTION

Euler's goniometers or cradles are standard devices in X-ray and neutron diffractometry, especially for single-crystal diffraction. In general, a two-circle Euler's cradle or goniometer provides a specimen holder rotatable about two turning circles (i.e. in two mutually perpendicular planes, namely the phi-circle and the chi-circle) for determining the structure of a crystal whereby the rotational movement in each plane is provided generally by respective stepper motors.

Examinations of crystal structure have turned out to be especially interesting at low or cryogenic temperatures so that low-temperature devices have been developed for this purpose.

Consequently, Euler goniometers of considerable size are known in which a cryostat for cooling the test samples, in particular by using liquid helium, is mounted on the phi-circle and is swingable through a given, usually limited angle.

Such Euler goniometers, however, have proven to be too bulky and, in particular, provide rotational possibilities only within a very limited angle range.

OBJECTS OF THE INVENTION

It is thus the principal object of our invention to provide an improved Euler goniometer obviating the aforestated drawbacks.

Another object of this invention is to provide a highly versatile improved Euler cradle or goniometer for two-circle X-ray or neutron diffractometry.

In particular, it is an object of the present invention to provide an Euler's goniometer which permits of full-circle diffractometry at low temperature.

SUMMARY OF THE INVENTION

We realize these objects, according to the invention, by providing an Euler goniometer having a casing so as to provide a chamber containing a coolant and receiving two-circle support, that is to say a support rotatable through 360° of both the chi-circle and the phi-circle, arranged within the chamber. The rotation is provided by respective driving means in the form of stepping motors which are also accommodated within the chamber.

The turning circles about which as test sample is rotated are each defined by a worm wheel of Be-Cu bronze or red brass provided with a toothed profile around its circumference which, according to another feature of our invention, is coated with a sliding varnish improving the sliding properties. Meshing with the toothed profile of each worm wheel is a Be-Cu bronze or red brass worm which is driven by a respective stepper motor so as to rotate the worm wheel in a predetermined manner. The preferred lubricant coating is a graphite-molybdenum sulfide composition in an inorganic, e.g. a silicone, binder. These compositions have been found to be especially important for operation at cryogenic temperature (i.e. to guarantee smooth action and avoid embrittlement).

Since the turning circles and the driving means are arranged within the test chamber and, consequently, the entire Euler goniometer can be integrated within the cryostat, an overdimensioning of the turning circles is avoided and rotational movement about 360° is possible.

BRIEF DESCRIPTION OF THE DRAWING

The above and other objects, features and advantages of our present invention will become more readily apparent from the following description with reference to the accompanying diagrammatic drawing, in which.

SPECIFIC DESCRIPTION

Figure 1:
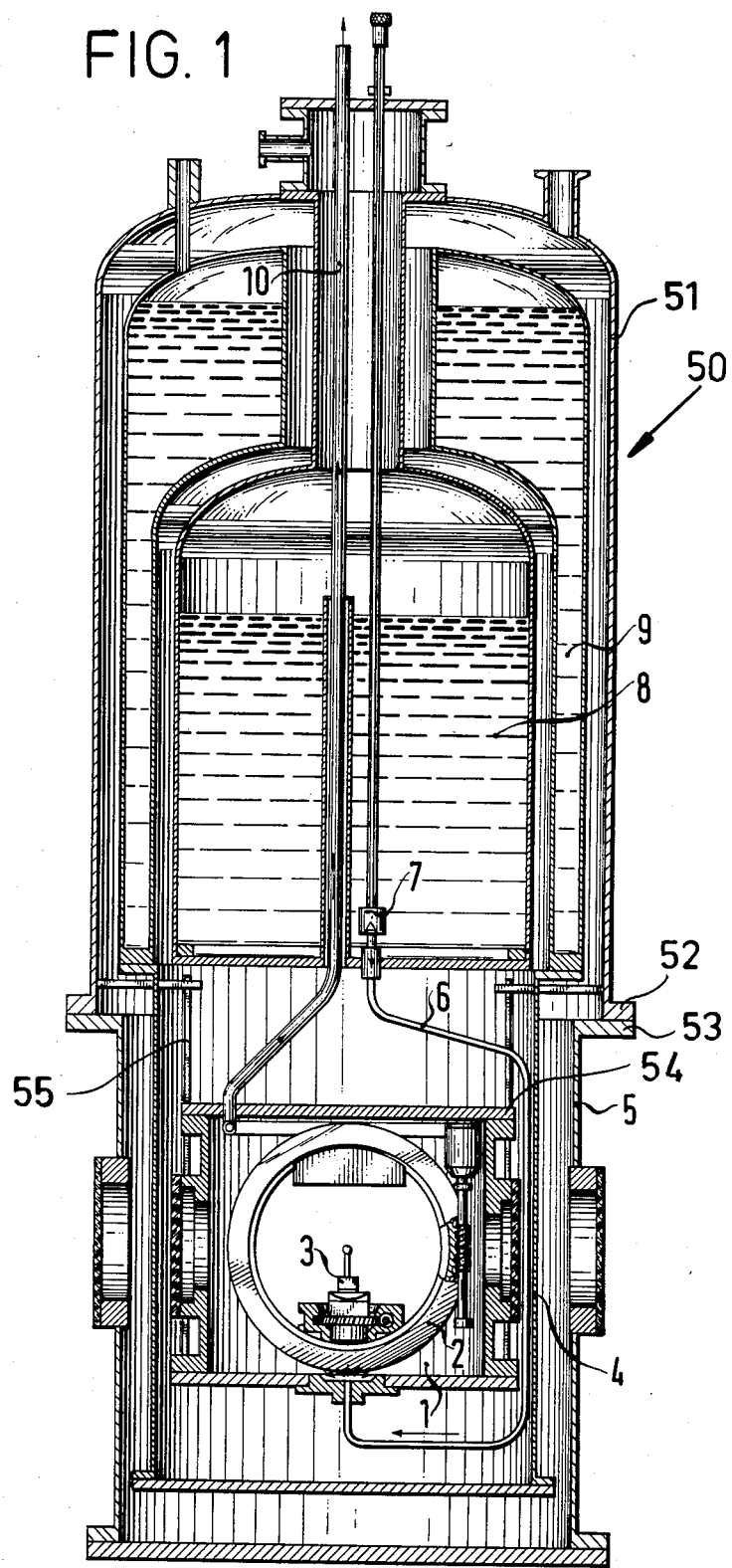
FIG. 1 is a schematic vertical section which illustrates a cryostat provided with an Euler's goniometer according to the invention.

Referring firstly to FIG. 1, there is shown a cryostat generally characterized by reference numeral 50. The cryostat 50 has an outer evacuated-wall casing 51 whose interior accommodates a reservoir 8 which contains liquid helium and is surrounded by a reservoir 9 filled with liquid nitrogen.

At its lower extremity, the casing 51 is provided with a flange portion 52 which is connected to a flange 53 of a vacuum jacket 5. Coaxially arranged at a distance to the jacket 5 and surrounded by the latter is a radiation shield 4 which together with the vacuum jacket 5 reduces the heat flow from outside.

Surrounded by the radiation shield 4 is an Euler goniometer or cradle 2 provided with a goniometer head 3 and having a casing 54 which is fixed to the outer casing 51 via fastening rods 55. The casing 54 defines an interior test chamber 1 communicating with the reservoir 8 via a capillary tube 6 through which the liquid helium is supplied by means of a needle valve 7 to the chamber 1. Helium gases as generated are discharged through pipe 10 whose one end projects through the casing 54 into the chamber 1 and extends along the cryostat 50 towards the outside.

In order to maintain a sufficiently low temperature of the helium so as to remain in the liquid state, a certain level of liquid helium is adjusted within the chamber 1 and kept constant by means of a level-measuring device (not shown) which thus controls the supply of helium from the reservoir into the chamber 1. Advantageously, the level of the liquid helium is adjusted to a level just below the crystal sample during radiation with neutrons. In addition, the temperature of the vaporized helium within the chamber 1 can be adjusted by an electric heating unit (not shown). Thus, experiments are possible at low temperatures controlled between liquid helium temperature and room temperature.

Figure 3:
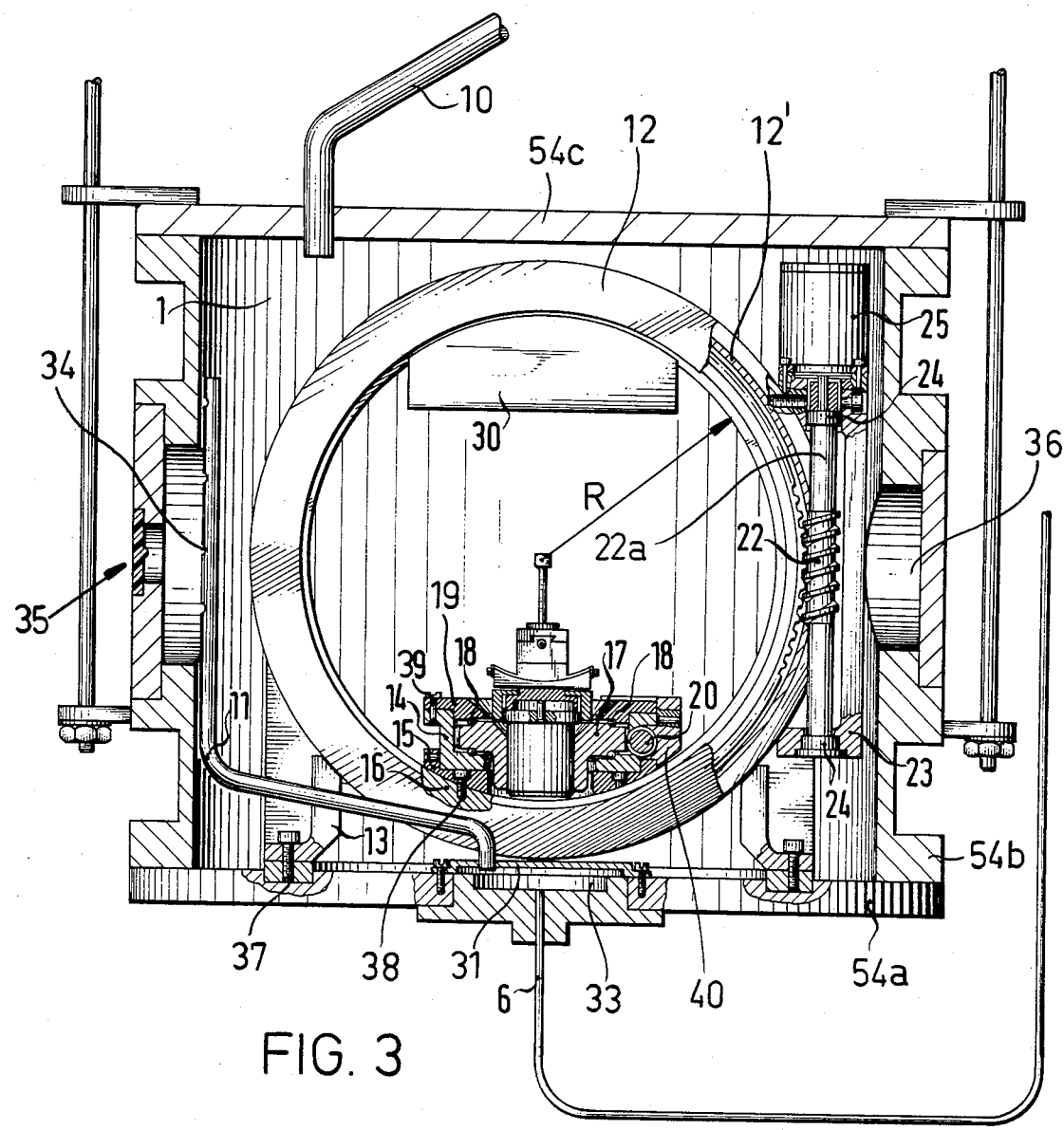
FIG. 3 is a sectional view in greater detail of an Euler's goniometer according to the invention.

Turning now to FIG. 3 which shows further detail of the Euler balance 2, the casing 54 has a bottom flange 54a, a chamber wall 54b connected to the flange 54a and a cover 54c fixed to the wall 54b. Projecting through the cover 54c is the pipe 10 for allowing helium gases to be discharged. At its center portion, the bottom flange 54a is connected via screw 32 to a plate 31 so as to define a space 33 into which one end of the tube 6 is guided to supply liquid helium from the reservoir 8. Projecting through the plate 31 into the space 33 is also a distributor pipe 11 which extends in vicinity of the chamber wall 54b and is provided with a plurality of openings 34 facing the wall 54b. Accordingly, the liquid helium is supplied via tube 6 and pipe 11 and eventually is sprayed through the openings 34 onto the wall 54b so as to guarantee a gradual large-area cooling and to prevent thermal stresses during the cooling.

Spaced around its circumference the chamber wall 54b is further provided with a plurality of aluminum neutron windows 35 having a height of 20 mm. In addition, the chamber wall 54b is provided at one side with a glass window 36 of 46 mm diameter for allowing visual observation and laser adjustments of the sample crystal inside the chamber 1. The glass window 36 can also serve for an in situ radiation of the crystal with laser beams at low temperatures.

Fixed to the bottom flange 54a via respective screw connections 37 are supports 13 for supporting a circular housing 12 of the Euler balance 2. Extending coaxially with the housing 12 and supported therein in a rotatable manner by interposed (not shown) balls is a worm wheel 16 provided with a toothed profile along its circumference. The worm wheel 16 cooperates with a worm 22 which is supported in a respective holder 23 via beryllium-copper (BeCu)-ball bearings 24. Connected to the holder 23 at its upper extremity is a stepper motor 25 which cooperates with the worm 22 via a coupling so as to provide the rotation of the crystal about the chi-circle 12'.

Fixed to the worm wheel 16 via screw connections 38 is a mounting 15 which supports an essentially L-shaped housing 14 that has an open top closed by a lid 19. Arranged between the housing 14 and the lid 19 is an inverted L-shaped worm wheel 17 which is rotatably supported via balls 18 interposed between the worm wheel 17 and the housing 14 and the worm wheel 17 and the lid 19. The connection between the lid 19 and the casing 14 is provided via screw connections 39.

The worm wheel 17 is provided along its circumference with a toothed profile which cooperates with a worm (driven by motor 21) extending at an angle, especially perpendicular, to the worm 22 and arranged at one side of the worm wheel 17. The worm 22 is housed in a holder 40 and driven as well as stopped by a stepper motor 25 (see FIG. 2) so as to provide the rotation of the crystal sample about the phi-circle 14'.

The holders 23, 40 for supporting the driving means of the chi-circle 12' and phi-circle 14' extend tangentially with respect to the associated turning circle.

In order to prevent brittleness of the material at especially low temperatures and upon consideration of different contractions during the cooling, the worms 20, 22 as well as the worm wheels 16, 17 are made of BeCu-bronze or red brass. For providing sufficient sliding, the toothed profiles of the worm wheels 16, 17 are coated with a lining, preferably with a molybdenum disulfide sliding varnish available under the trademark "Molykote 321" on the basis of graphite and $MoS_2$ in a ratio of 1:2 combined with an inorganic (e.g. silicone) binder.

In addition, the housings 12, 14 as well as the lid 19 are preferably made of red brass by centrifugal casting in order to prevent thermal stres and anisotropic thermal contraction. The ball bearings of the stepper motors 21, 25 and of the worm shafts as well as the balls are also made of BeCu. It is, however, also suitable to provide the ball bearings of conventional ball-bearing steel and to coat the balls and running surfaces with a dry sliding agent like "Wolfratherm". To avoid corrosion, the stepper motors 21, 25 are provided with nickel-plated rotors.

Connected to the casing 12 is a counterweight 30 for the arrangement constituting the phi-circle 14'.

Figure 2:
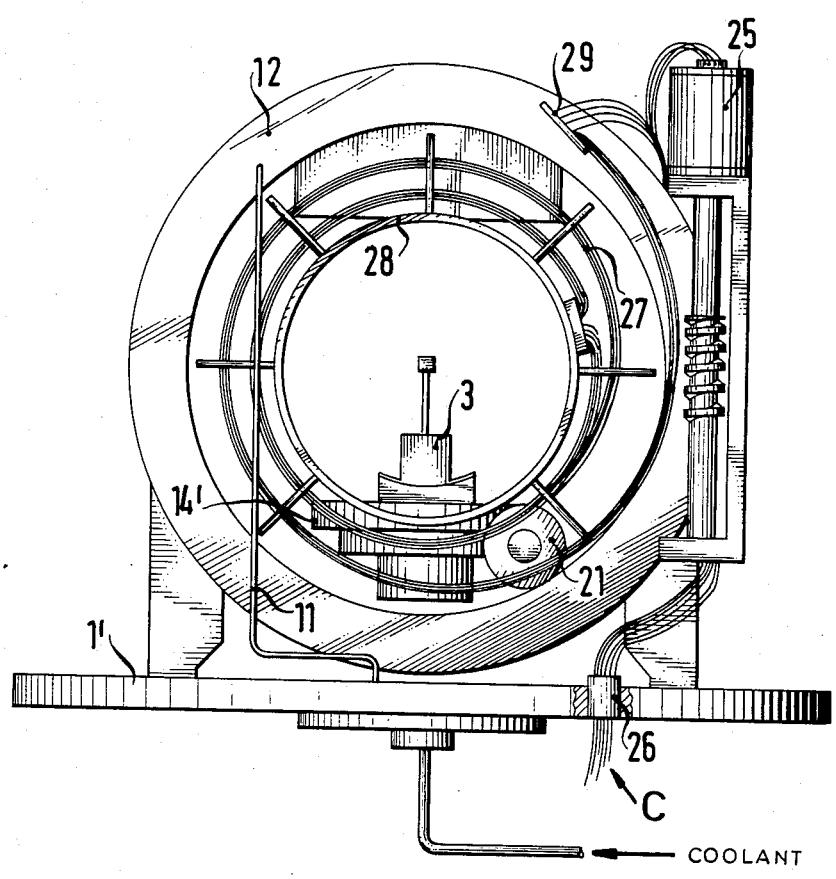
FIG. 2 is a detail vertical section, also in highly diagrammatic form, of the Euler's goniometer according to the invention showing the electrical connections.

We turn now to FIG. 2 in which the cabling and power supply of the stepper motors 21, 25 is shown for providing the rotation about the chi-circle 12' and the phi-circle 14'. Accordingly, the cables C are guided through a cable duct 26 of the bottom flange 54a. The cables for the stepper motor 25 are directly linked thereto while the cables for the stepper motor 21 are connected thereto via a coil spring 27 along which the cables are guided.

The coil spring 27, which is made of BeCu, has one end fixed to a mounting 29 arranged at the chi-circle 12' while its other end leads to the stationary stepper motor 21. In addition, a holder 28 is arranged to movably retain the coil spring 27 as well as the respective cables for the stepper motor 21 in its position.

In order to prevent a jamming of the cables during rotation about the chi-circle and so as not to obstruct the radiation space or to obscure the field of view, the coil spring 27 and the holder 28 extend coaxially to the chi-circle 12' but are arranged at a distance to the midplane of the Euler goniometer 2.

In the exemplified embodiment, the chi-circle 12', i.e. the worm wheel 16 constituting the chi-circle 12', has an inner radius R of 87 mm. The goniometer head 3 used in the Euler goniometer 2 can have a height up to 52 mm and is mounted with an ACA-standard screw thread.

The stepper motors 21, 25 are identical and provide a rotation about 1.8° per motor step. The worm drive 20 for the rotation about the phi-circle 14' is provided with a gear ratio of 1:180 while the worm drive 22 for the rotation about the chi-circle 12' is provided with a gear ratio of 1:360. Consequently, the crystal sample is rotated about the chi-circle 12' by 0.005° per step (or pulse) while being rotated about the phi-circle 14' by 0.01° per step (or pulse). As verified through measurements, inaccuracies are within ±0.01° in chi and ±0.02° in phi can be set. Zero-position for the rotation about 360° in both directions is provided by a microswitch (not shown).

In the exemplified embodiment, the chamber 1 has a volume of approximately 15 l. The Euler goniometer 2 can be operated in a temperature range between 4° K. up to room temperature (about 300° K.). For controlling the temperature in the chamber 1 within which the Euler goniometer 2 as well as the crystal sample are located, a controllable heating coil (not shown) is arranged at the bottom flange 54a. In addition, two feeler gauges (not shown) are provided at the lower and upper section of the chi-circle 12'.

The Euler goniometer 2 was tested by neutron diffraction. Thus, a beam of neutrons was directed onto a crystal sample which is rotated about the chi-circle 12' and the phi-circle 14'. The chamber 1 was filled with liquid helium to a level below the beam plane. During this test at 4.2° K. over two days, the mechanics of the Euler goniometer proved to be flawless. Analogous tests with liquid nitrogen over several days led to the same result. The rotations about the chi-circle and the phi-circle were optically controlled through the glass window. Through reflectance measurements by reflecting an incident laser beam from a mirror arranged in sample position, the precision of the stepwise rotational movements was verified.

We claim:

1. An Euler's two-circle goniometer for cryogenic, X-ray and neutron diffractometry, comprising:
    a casing defining a chamber containing a coolant;
    a specimen holder in said chamber for a test sample;
    first and second rotating means each arranged within said chamber and operatively connected with said specimen holder for turning said test sample about a first and a second turning circle in mutually perpendicular planes; and
    a respective stepper motor in said chamber connected to each of said rotating means for actuating the latter so as to turn the test sample about said turning circles.

2. The Euler's goniometer defined in claim 1 wherein said first and second rotating means each includes a stationary housing and a worm wheel coaxially extending within said housing and having a toothed profile along its circumference, said worm wheel of said first rotating means being arranged at an angle to said worm wheel of said second rotating means.

3. The Euler's goniometer defined in claim 2, further comprising ball bearings for supporting said worm wheels within said housing in a rotatable manner.

4. The Euler's goniometer defined in claim 2 wherein said stepper motors are connected to first and second worms for driving the latter in a stepwise manner.

5. The Euler's goniometer defined in claim 4 wherein each of said worms and each of said worm wheels is made of beryllium copper (BeCu)-bronze.

6. The Euler's goniometer defined in claim 4 wherein each of said worms and each of said worm wheels is made of red brass.

7. The Euler's goniometer defined in claim 2 wherein said toothed profile of each of said worm wheels is coated with a sliding varnish.

8. The Euler's goniometer defined in claim 7 wherein said sliding varnish contains graphite and molybdenum disulfide in a ratio of 1:2 with an inorganic binder.

9. The Euler's goniometer defined in claim 2 wherein each of said housings and each of said worm wheels is of centrifugally cast red brass.

10. The Euler's goniometer defined in claim 3 wherein said ball bearings include a plurality of balls interposed between said worm wheels and said housings.

11. The Euler's goniometer defined in claim 10 wherein said balls are made of BeCu bronze.

12. The Euler's goniometer defined in claim 4, further comprising ball bearings for each of said stepper motors and each of said worms, said ball bearings being made of BeCu bronze.

13. The Euler's goniometer defined in claim 4 wherein each of said stepper motors has a nickel-plate rotor.

14. The Euler's goniometer defined in claim 1, further comprising guiding means for leading cables to said stepper motors nd including a coil spring arranged coaxially to said first turning circle at a distance to the mid plane of said chamber, the cables being fixed along said coil spring so that a jamming thereof during rotation about said first turning circle is prevented.

15. The Euler's goniometer defined in claim 14 wherein said guiding means further includes a holder for movably retaining said coil spring in its position.

16. The Euler's goniometer defined in claim 1 wherein said casing has a chamber wall, and further comprising a pipe for supplying a coolant into said chamber, said pipe extending adjacent to said chamber wall and having a plurality of openings directed toward said chamber wall.

* * * * *